United States Patent
Nguyen

(10) Patent No.: US 6,569,454 B2
(45) Date of Patent: May 27, 2003

(54) SIMPLE TABLET COMPRESSION USING GELATIN

(76) Inventor: Minh Van Nguyen, 905 S. Webster Ave., #15, Anaheim, CA (US) 92804

( * ) Notice: Subject to any disclaimer, the term of this patent is extended or adjusted under 35 U.S.C. 154(b) by 0 days.

(21) Appl. No.: 09/792,932

(22) Filed: Feb. 27, 2001

(65) Prior Publication Data

US 2002/0164370 A1 Nov. 7, 2002

(51) Int. Cl.⁷ .................................................. A61K 9/20
(52) U.S. Cl. ........................ 424/464; 424/465; 514/960; 514/774
(58) Field of Search ................................. 424/464, 465, 424/468, 469, 470

(56) References Cited

U.S. PATENT DOCUMENTS 5,738,872 A * 4/1998 Ortyl et al. .................. 424/452
6,068,854 A * 5/2000 Wunderlich et al. ........ 424/464

* cited by examiner

*Primary Examiner*—James M. Spear

(57) ABSTRACT

The present invention comprises a method of tablet preparation. The invention provides a simple and cost effective method to compress good tablets.

10 Claims, No Drawings

SIMPLE TABLET COMPRESSION USING GELATIN

FIELD OF THE INVENTION

This invention relates to tablet preparations.

BACKGROUND OF THE INVENTION

In addition to the active ingredient(s), a tablet basically contains: (1) diluent, (2) binder, (3) disintegrator, and (4) lubricant.

Diluent is a substance or a mixture of substances added to a tablet to increase the bulk in order to make the tablet a practical size for compression.

Binder is a substance or a mixture of substances added to a tablet to impart a cohesiveness to the tablet formulation which insures the tablet remaining intact after compression.

Disintegrator is a substance or a mixture of substances added to a tablet to facilitate its breakup or disintegration after administration.

Lubricant is a substance or a mixture of substances added to a tablet to improve the flowability and to prevent adhesion of the tablet material to the surface of the dies and punches, reduce interparticle friction, and facilitate the ejection of the tablets from the die cavity.

There are currently three general methods of tablet preparation: (1) wet-granulation method, (2) dry-granulation method, and (3) direct compression. All three methods have disadvantages.

Wet-granulation method is the most widely used method. Its popularity is due to the greater probability that the granulation will meet all the physical requirements for the compression of good tablets. Its chief disadvantages are the number of separate steps involved and the time and labor necessary to carry out the procedure. The steps involved in the wet-granulation method are: (1) weighing, (2) mixing, (3) granulation, (4) screening the damp mass after granulation, (5) drying (6) dry screening (7) lubrication, and (8) compression.

Dry-granulation method is generally used when tablet ingredients are sensitive to moisture or are unable to withstand elevated temperatures during drying. This method eliminates a number of steps but still includes (1) weighing, (2) mixing, (3) dry granulation, (4) dry screening, (5) lubrication, and (6) compression. However, this method requires that the tablet ingredients must have sufficient inherent binding or cohesive properties for dry granulation.

Direct compression consists of compressing tablets directly from ingredients without wet or dry granulation. This method comprises only three steps: (1) weighing, (2) mixing, and (3) compression. However, it has two major disadvantages: (1) the active ingredients must possess inherent binding and cohesive properties, and/or (2) the diluents and/or binders must be capable of imparting the compressible characteristics. To acquire these properties, the ingredients must be subjected to preprocessing step such as wet granulation, dry granulation, or other granulation processes such as spheronization, spray drying, and crystallization.

SUMMARY OF INVENTION

The present invention discloses a new method of tablet preparation which is very simple and cost effective.

The method of the present invention consists of compressing tablets directly from powdered materials without modifying the physical nature of the materials using gelatin. All ingredients used in this method do not have to undergo preprocessing step such as wet granulation, dry granulation, or other granulation processes such as spheronization, spray drying, and crystallization.

An aqueous solution of gelatin has often been used in wet granulation. However, its dry form, powder or granules, has never been directly used in tablet compression.

It is an object of this invention to provide a simple method of preparing tablets in which gelatin, in its dry form, with its strong binding, cohesive, and hydrophillic properties, can be utilized as tablet diluent, and/or binder, and/or disintegrator.

The method of tablet preparation in this invention comprises only three simple steps: (1) weighing, (2) mixing, and (3) compression.

DETAIL DESCRIPTION OF THE INVENTION

The following discussion details procedure of the tablet preparation using gelatin.

Gelatin used in this invention can be powder or granules and in concentrations from 0.1% to 99.9% of the tablet weight.

STEP 1—WEIGHING: Active ingredient(s), gelatin, and other ingredient(s) are accurately weighed.

STEP 2—MIXING: Active ingredient(s), gelatin, and other ingredient(s) are added, one item at a time, into a suitable blender and mix for an appropriate length of time.

STEP 3—COMPRESSION: The mixture from STEP 2 is compressed into tablets.

In order to more clearly define the invention, the following examples of method of preparing tablets using gelatin at different concentrations are given. It is understood that these examples are considered as illustrative only and are not to be construed as limitations on the present invention.

EXAMPLE I

Gelatin is Used as Diluent, Binder, and Disintegrator

| Vitamin $B_{12}$ 6 mcg tablets | |
|---|---|
| Vitamin $B_{12}$, powder (active ingredient) | 0.006 mg/tablet |
| Gelatine, powder | 199.804 mg/tablet |
| Magnesium stearate, powder (lubricant) | 0.190 mg/tablet |
| Total Weight | 200.000 mg/tablet |

Procedure

1. Accurately weigh vitamin $B_{12}$, gelatin, and magnesium stearate.
2. Mix vitamin $B_{12}$ and gelatin in a suitable blender for 15 minutes. Add magnesium stearate and mix for additional 5 minutes.
3. Compress.

| Tablet properties | |
|---|---|
| Size/Form: | 0.291" round tablet |
| Weight: | 200.0 mg |
| Hardness: | 5.0 Kg |
| Friability: | Less than 1.0% |
| Disintegration: | 1 minute |

EXAMPLE II

Gelatin is Used as Diluent, Binder, and Disintegrator

| Vitamins-minerals-herbs tablets | |
|---|---|
| Thiamin HCl, powder (active ingredient) | 10.00 mg/tablet |
| Niacinamide, powder (active ingredient) | 20.00 mg/tablet |
| Pyridoxine HCl, powder (active ingredient) | 10.00 mg/tablet |
| Calcium carbonate, powder (active ingredient) | 525.00 mg/tablet |
| Magnesium oxide, powder (active ingredient) | 335.00 mg/tablet |
| Green tea, powder (active ingredient) | 10.00 mg/tablet |
| Korean ginseng, powder (active ingredient) | 20.00 mg/tablet |
| Gelatine, powder | 100.00 mg/tablet |
| Magnesium stearate, powder (lubricant) | 20.00 mg/tablet |
| Silicon dioxide, powder (lubricant) | 10.00 mg/tablet |
| Total Weight | 1060.00 mg/tablet |

Procedure

1. Accurately weigh thiamin HCl, niacinamide, pyridoxine HCl, calcium carbonate, magnesium oxide, green tea, Korean ginseng, gelatin, magnesium stearate, and silicon dioxide.
2. Add thiamin HCl, niacinamide, pyridoxine HCl, calcium carbonate, magnesium oxide, green tea, Korean ginseng, gelatin, one item at a time, in a suitable blender and mix for 15 minutes. Add magnesium stearate and silicon dioxide and mix for additional 5 minutes.
3. Compress.

| Tablet properties | |
|---|---|
| Size/Form: | ⅝" round tablet |
| Weight: | 1060.0 mg |
| Hardness: | 8.0 Kg |
| Friability: | Less than 1.0% |
| Disintegration: | 10 minutes |

EXAMPLE III

Gelatin is Used as Diluent and Binder

| Potassium chloride 30 mg tablets | |
|---|---|
| Potassium chloride, powder (active ingredient) | 30.0 mg/tablet |
| Gelatin, powder | 160.0 mg/tablet |
| Croscarmelose sodium, powder (disintegrator) | 2.0 mg/tablet |
| Talc, powder (lubricant) | 5.0 mg/tablet |
| Magnesium stearate, powder (lubricant) | 3.0 mg/tablet |
| Total Weight | 200.0 mg/tablet |

Procedure

1. Accurately weigh potassium chloride, gelatin, croscarmelose sodium, talc, and magnesium stearate.
2. Add potassium chloride, gelatin, and croscarmelose sodium, one item at a time, in a suitable blender and mix for 15 minutes. Add talc and magnesium stearate and mix for additional 5 minutes.
3. Compress.

| Tablet properties | |
|---|---|
| Size/Form: | 0.291" round tablet |
| Weight: | 200.0 mg |
| Hardness: | 7.0 Kg |
| Friability: | Less than 1.0% |
| Disintegration: | 2 minutes |

EXAMPLE IV

Gelatin is Used as Binder

| Calcium carbonate 1250 mg tablets | |
|---|---|
| Calcium carbonate, powder (active ingredient) | 1250.0 mg/tablet |
| Gelatine, powder | 80.0 mg/tablet |
| Stearic acid, powder (diluent) | 40.0 mg/tablet |
| Microcrystalline cellulose, powder (diluent) | 35.0 mg/tablet |
| Croscarmelose sodium, powder (disintegrator) | 35.0 mg/tablet |
| Magnesium stearate, powder (lubricant) | 30.0 mg/tablet |
| Silicon dioxide, powder (lubricant) | 15.0 mg/tablet |
| Total Weight | 1485.0 mg/tablet |

Procedure

1. Accurately weigh calcium carbonate, gelatin, stearic acid, microcrystalline cellulose, croscarmelose sodium, magnesium stearate, and silicon dioxide.
2. Add calcium carbonate, gelatin, stearic acid, microcrystalline cellulose, croscarmelose sodium, one item at a time, in a suitable blender and mix for 15 minutes. Add magnesium stearate and silicon dioxide and mix for additional 5 minutes.
3. Compress.

| Tablet properties | |
|---|---|
| Size/Form: | 0.750 × 0.312" caplet |
| Weight: | 1485.0 mg |
| Hardness: | 8.0 Kg |
| Friability: | Less than 1.0% |
| Disintegration: | 5 minutes |

EXAMPLE V

Gelatin is Used as Disintegrator

| Methenamine 500 mg tablets | |
|---|---|
| Methenamine, powder (active ingredient) | 500.0 mg/tablet |
| Gelatine, powder | 0.5 mg/tablet |
| Magnesium stearate, powder (lubricant) | 4.5 mg/tablet |
| Total Weight | 505.0 mg/tablet |

Procedure

1. Accurately weigh methenamine, gelatin, and magnesium stearate.
2. Mix methenamine and gelatin in a suitable blender for 15 minutes. Add magnesium stearate and mix for additional 5 minutes.

3. Compress.

| Tablet properties | |
|---|---|
| Size/Form: | ⅜" round tablet |
| Weight: | 505.0 mg |
| Hardness: | 5.0 Kg |
| Friability: | Less than 1.0% |
| Disintegration: | 5 minutes |

Note: In this example, methenamine naturally possesses cohesive property which makes compression without binders possible. However, if gelatin is absent, the disintegration would take longer than 30 minutes.

I claim:

1. A simple method for directly compressing tablets, consisting of compressing tablets directly from powdered materials without modifying the physical nature of the materials using gelatin wherein said powdered materials do not undergo a preprocessing step.

2. The method of claim 1, wherein said gelatin can be powder or granules.

3. The method of claim 1, wherein said gelatin is used in concentrations from 0.1% to 99.9% of the tablet weight.

4. The method of claim 1, wherein said gelatin is used as diluent, binder, and disintegrator.

5. The method of claim 1, wherein said gelatin is used as diluent and binder.

6. The method of claim 1, wherein said gelatin is used as diluent and disintegrator.

7. The method of claim 1, wherein said gelatin is used as binder and disintegrator.

8. The method of claim 1, wherein said gelatin is used as diluent.

9. The method of claim 1, wherein said gelatin is used as binder.

10. The method of claim 1, wherein said gelatin is used as disintegrator.

* * * * *